United States Patent [19]

Borch

[11] Patent Number: 4,581,224

[45] Date of Patent: Apr. 8, 1986

[54] INHIBITION OF UNDESIRED EFFECT OF PLATINUM COMPOUNDS

[75] Inventor: Richard F. Borch, 4 Bromley Rd., Pittsford, N.Y. 14534

[73] Assignee: Regents of the University of Minnesota, Minneapolis, Minn.

[21] Appl. No.: 568,904

[22] Filed: Jan. 5, 1984

Related U.S. Application Data

[63] Continuation-in-part of Ser. No. 176,476, Aug. 8, 1980, Pat. No. 4,426,372.

[51] Int. Cl.[4] ............................................. A61K 31/27
[52] U.S. Cl. ..................................... 424/10; 514/476; 514/491; 514/974
[58] Field of Search .................. 424/10, 287; 514/476, 514/491, 974

[56] References Cited

U.S. PATENT DOCUMENTS 4,053,587 10/1977 Davidson et al. .................... 424/131
4,137,248 1/1979 Gale et al. ............................ 556/137

FOREIGN PATENT DOCUMENTS 1030528 5/1978 Canada.
1104578 7/1981 Canada.

OTHER PUBLICATIONS

Lin et al., C.A. vol. 91 (1979) 91:117,166d.
Borch et al.; Proc. Natl. Acad. Sci. (USA), vol. 76, No. 12, pp. 6611–6614 (1979).
Thorn et al., *The Dithiocarbomates and Related Compounds*, Elsevier, Amsterdam, 1962, Chapters 3 and 8.
Chem. Abs. 91:117166d (1979).
Einhorn et al., *NEJM* 300: 289–291 (1979).
Borch et al., Proc. Natl. Acad. Sci. USA, and 77: 5441 (1980).
Cancer Treatment Reports 62: 1431,1433–1444, 1475–1483, 1493–1502, 1527–1531 (1979).
Borch et al., *Analyt. Letters*, 12(B8): 917 (1979).
Sunderman, *Ann. Clin., Res.* 3:182 (1971).
National Formulary XIV, 14th Ed., pp. 237–238 (1979).
New Ethicals Catalogue, Dec. 1978, p. A8.
Physician' Desk Reference, 1965 ff., "Antabuse".
Research and Invention, Winter 1972 and 1977–1978.
List of references cited in Great Britain (attached) and copies thereof.
Slater et al., *J. Clin. Hematol. Oncol.* 7:534–546 (1977).
Connors, *Advances in Antimicrobial and Antineoplastic Chems. Therapy*, University Park Press, Baltimore 1972, vol. 2, pp. 237–238.
Filipski et al., *Science*, 204:181–183 (1979).
Cafruny, Pharmacological Rev. 20:89–116 (1968).
Burchenol et al., *Viochimie* 60:961–965 (1978).
Cafruny et al., *J. Pharmacol Exp. Ther.*, 117:101 (1956).
Dieke et al., *J. Pharmacol. Exp. Ther.* 83:195–202 (1948).
*AACR Abstracts* (Higby et al) 16:523A (1975).
Sunderman, *Ann. Clin. Lab. Sci.*, 9:1–10 (1979).
Hayes et al., *Cancer* 39:1372–1381 (1977).
Cvitkovic et al., *Cancer* 39:1357–1361 (1977).
Astwood, *J. Pharmacol.Exp.Ther.*, 78:79–91 (1943).

Primary Examiner—Allen J. Robinson
Attorney, Agent, or Firm—Connolly and Hutz

[57] ABSTRACT

Dithiocarbamic compounds, administered about 0.5 to about 6 hours after Pt compounds, have been found to counter the toxicity of the platinum in multi-cellular organisms (e.g. mammals). For example, neoplastic growths in mammals can be treated with cis-diamine or cis-diamine Pt(II) complexes with greatly lessened risk of nephrotoxicity, bone marrow toxicity, or damage to the digestive system of the mammal, provided the dithiocarbamic compound is timely (and preferably parenterally) administered. Particularly effective dithiocarbamic compounds are monomeric (e.g.

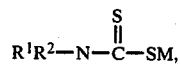

where M is a pharmaceutically acceptable cation and $R^1$ and $R^2$ are lower aliphatic (or cycloaliphatic or heterocycloaliphatic groups) or, less preferably, dimeric, e.g.

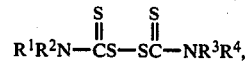

wherein $R^1$ and $R^2$ are as defined previously, and $R^3$ and $R^4$ are defined in the same manner as $R^1$ and $R^2$. These dithiocarbamic compounds do not significantly reduce the desired effect of the Pt(II) compounds (particularly when the dithiocarbamic compound is intravenously admininstered), despite their effectiveness in reducing harmful side effects.

10 Claims, No Drawings

INHIBITION OF UNDESIRED EFFECT OF PLATINUM COMPOUNDS

This application is a continuation-in-part of my copending application Ser. No. 176,476, filed Aug. 8, 1980, now U.S. Pat. No. 4,426,372, issued Jan. 17, 1984.

TECHNICAL FIELD

This invention relates to a method for inhibiting the ability of platinum(II) complexes to bond strongly to certain substrates (such as enzymes, particularly enzymes having mercapto or sulfhydryl groups) without eliminating the ability of these complexes to bind to certain other substrates, such as cellular desoxyribonucleic acid (DNA). This invention also relates to inhibition of the toxicity of platinum (II) complexes which, for transport reasons or the like are administered initially as a corresponding platinum(IV) species with easily removed axial substituents. An aspect of this invention relates to a method for inhibiting platinum toxicity without eliminating the desired physiological efficacy of the platinum(II) or platinum(IV) compound. Still another aspect of this invention relates to a method for inhibiting platinum(II) toxicity (e.g., nephrotoxicity, bone marrow toxicity, etc.) in live mammal being treated with a physiologically active platinum(II) or (IV) compound. Still another aspect of this invention related to a method for forming a complex of platinum-(II) and a dithiocarbamic compound in situ in the presence of live cellular material (e.g., in vivo).

The invention described herein was made in the course of work under a grant or award from the Department of Health, Education and Welfare.

PRIOR ART

Recent studies have shown that a variety of square planar platinum(II) complexes have beneficial physiological properties, despite a strong tendency to be toxic toward living organisms, particularly organisms having digestive systems or kidneys or enzymes capable of complexing with platinum(II). The physiological or pharmacological utility of platinum(II) complexes stems largely from their ability to inhibit harmful organisms or enzymes and neoplastic cell growth. Accordingly, investigators in this field have been looking for ways of utilizing the platinum(II) therapeutically without causing excessive damage to healthy cells or tissue. There is evidence indicating that the mechanism for platinum(II) activity against, for example, neoplastic cells is different from the mechanism of nephrotoxicity, damage to the digestive system or to bone marrow, and other undesirable side effects. Similar considerations apply to platinum(II) compounds administered initially as platinum(IV) complexes having easily removed groups in the axial positions, e.g., OH or $H_2O$. These platinum(IV) complexes are believed to function as platinum(II) compounds at the site of therapeutic action in vivo. If indeed the mechanism for the useful activity of these compounds is different from the mechanisms of the damaging side effects, opportunities should exist for mitigating the side effects without detracting significantly from the desired physiological effects. Noting that the most serious permanent damage from platinum-(II) compounds such as cis-dichlorodiammineplatinum-(II) is typically found in the kidneys of mammals, a typical practice of cis-dichlorodiammineplatinum(II) administration makes use of mannitol diuresis, coupled with intravenous prehydration, which has been found, for example, to ameliorate acute toxicity in both dogs and humans. See Cvitkovic et al, CANCER 39:1357 (1977) and and Hayes et al, CANCER 39:1372 (1977). In addition, a number of thio reagents have been examined for their effects upon platinum toxicity, including cysteine, penicillamine, cysteimine, and N-acetylcysteine. Similar experiments have been conducted with thiourea. The following literature references are believed to be representative of the experimental work with thiols and thiourea:

Slater et al, *J. Clin. Hematol. Oncol.* 7:534 (1977).
Connors, T. A. in *Advances in Antimicrobial and Antineoplastic Chemotherapy*, Volume 2, University Park Press, Baltimore, Md., 1972, pages 237–238.
Higby et al, *Proc. Am. Assoc. Cancer Res.* 16:523A (Abstract) (1975).
Burchenal, J. H. et al, *Biochimie* 60, 961–965 (1978).
Dieke, S. H. et al, *J. Pharmacol. Exp. Ther.* 83, 195–202 (1948).
Atwood, E. B., *J. Pharmacol. Exp. Ther.* 78, 79–91 (1943).
Filipski, J., et al, *Science* 204, 181–183 (1979).

These sulphur-containing compounds were presumably selected because of the strong ability of both thiols and thiocarbonyls to bond to platinum (II), even to the point of displacing existing ligands and leaving groups. These platinum-binding sulphur compounds are sometimes referred to as "rescue agents", since the hope of the investigators was that the platinum binding effect would "rescue" the organism from kidney damage and the like. Unfortunately, no beneficial effects have so far been reported in those experiments in which a thiol was administered after the platinum (II). Some benefit was reported when cysteine and penicillamine were given before the platinum (II). However, there is also some evidence indicating that cysteine and penacillamine may have the potential to bind to plasma platinum and hence reduce its chemotherapeutic effect. Decreased efficacy of platinum (II) has also been observed in the case of thiourea when the thiourea was administered prior to the platinum (II). Thiourea has been reported to inhibit thyroid hormone production and thus may have other drawbacks.

The chemistry of platinum and the use of platinum in biological systems are both vast fields. It would be difficult to provide even a representative sampling of patents and literature relating to platinum(II) compounds as antitumor agents. The same could be said regarding the art of platinum complex formation using sulphur-containing ligands. An excellent series of papers regarding platinum treatment of tumors and resulting side effects appears in Cancer Treatment Reports, Volume 63 (1979), beginning at page 1433. U.S. Patents of interest regarding platinum treatment of neoplastic cells and viruses include U.S. Pat. Nos. 4,053,587 (Davidson et al), issued Oct. 11, 1977, and 4,137,248 (Gale et al), issued Jan. 30, 1979. The chemical compound cis-dichlorodiammineplatinum(II) is commercially available from Bristol Laboratories Division of Bristol Myers Company of Syracuse, N.Y., U.S.A. as an antineoplastic agent typically indicated for palliative therapy for metastatic testicular and ovarian tumors.

SUMMARY OF THE INVENTION

It has now been found that there is a class of dithiocarbamic monomers and dimers which can inhibit the ability of platinum(II) compounds to bond irreversibly to useful substrates without eliminating the desirable effects of these compounds. For example, it has been found that nephrotoxicity of platinum(II) antitumor agents can be ameliorated without significantly interfering with the chemotherapeutic utility of these agents. The timing of the administration of the dithiocarbamic compounds used in this invention is of great importance. Administering the compounds prior to, coincidental with, or many hours after platinum(II) is likely to provide very little amelioration of the injurious side effects of the platinum. The preferred timing can be described in several ways, e.g. (1) as a period of time after platinum(II) administration (preferably about 0.5 to about 6 hours afterwards), (2) after a certain minimum and preferably before a certain maximum number of plasma half-lives of the platinum(II) (optimally after about 4 but before about 8 plasma half-lives), (3) after the desirable physiological effects of the platinum(II) have been initiated but prior to about 6 hours thereafter, (4) after the platinum(II) has begun to complex with cellular DNA but before the platinum has permanently and irreversibly damaged renal tubules, e.g. through complexing with —SH groups naturally occurring in the renal tubules (which is believed to result in inhibition of water and electrolyte reabsorption in the proximal tubule via coordination of platinum(II) to the —SH group of a membrane-bound transport enzyme). Presently published research findings, studied with the concepts of this invention in mind tend to suggest that these various ways of defining the preferred and optimum timing of the administration of the dithiocarbamic compounds are generally, even if not precisely, equivalant. The exact timing can depend to a degree on the type of platinum(II) compound, but depends to a greater degree upon the particular dithiocarbamic compound which is selected and the internal processes occurring within the biological system being treated. If for any reason it is more convenient or effective to administer platinum(II) with highly labile leaving groups in the axial positions (resulting initially in the formation of a platinum(IV) complex), the foregoing timing schemes are still applicable, because the active agent in vivo is still essentially a platinum(II) compound.

The preferred dithiocarbamic compounds have the structure

wherein $R^1$ and $R^2$ are the same or different and represent electron-donating lower aliphatic or lower cycloaliphatic radicals, or $R^1$ and $R^2$ taken together can form an aliphatic heterocyclic ring with the nitrogen atom, and M is selected from the group consisting of (1) hydrogen, (2) an electropositive, ionically bonded metal, in which case the remainder of said compound is negatively charged, and (3) the radical

$R^3$ and $R^4$ being defined in the same manner as $R^1$ and $R^2$.

The platinum complex can be administered in a generally conventional manner, although a single effective dose of platinum or discrete dosages administered several hours apart would be preferred over the continuous courses of intravenous administration typically recommended for the platinum(II) or (IV) antitumor agents presently in use or under investigation. The route of administration of the dithiocarbamic compounds is preferably tailored to deal with the rapid metabolism or degradation or inactivation of these compounds in acidic media, living biological systems, and other systems in which the dithiocarbarmate functional group

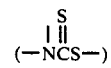

is converted to compounds such as carbon disulfide which have no utility in the context of this invention. Parenteral (e.g. intravenous or intraperitoneal) administration is ordinarily less subject to excessively rapid degradation of the dithiocarbamic compounds; surprisingly, it has been found that the intravenous route is the most effective on two counts. First, there appears to be less interference with the desired physiological effects of the platinum(II). Second, the dosage needed to inhibit nephrotoxicity is typically within the range of about 50 to 400 milligrams per kilogram of body weight, which is a significantly lower dosage than would be preferred for the intraperitoneal route.

Stated another way, this invention is considered to relate to a method for inhibiting the ability of the platinum(II) compound to bond strongly or irreversibly to useful enzymes or sulfhydryl (mercaptan) compounds without inhibiting its ability to complex with cellular DNA, and the method is carried out by permitting the platinum(II) to be exposed to cellular DNA first before the dithiocarbamic compound is administered. As noted previously, this invention is not bound by any theory. It is nevertheless theorized that, if a single dose of platinum(II) is administered intravenously on a short-course or almost instantaneous basis, it is likely that platinum-(II)-DNA complexes can form within cells (e.g. neoplastic cells) within about an hour after the dose enters the bloodstream. The optimum period of time for DNA complexing is believed to be more than one hour after platinum administration and more preferably after two hours. As noted previously, the administration of the dithiocarbamic compound preferably takes place within six hours of platinum(II) administration, 1.5–4 hours being the optimum time span allowed for good DNA complexing combined with good inhibition of nephrotoxicity.

DETAILED DESCRIPTION

The principles of this invention generally relate to a complex situation in which there is a necessity for reversing a platinum(II)/enzyme or platinum(II)/—SH interaction within about six hours of the time that the platinum becomes available for interaction with the enzymes or sulfhydryl groups and perhaps even within four hours of this platinum accessibility. To further complicate the situation, the typical reason for the accessibility to the platinum is that a chemotherapeutic platinum(II) complex has been administered to an organism or multicellular system, and the desired chemotherapeutic effect would be defeated if the platinum is simply chelated or otherwise rendered inactive before it has had an opportunity to interact with the targeted substrate. (The substrate "target" would typically be neoplastic cells, a pathogenic microorganism, a virus, or the like.) These first two conditions can generally be dealt with through careful timing, e.g. of the type described previously. That is, the platinum(II) can be administered first in essentially a single dose followed by administration of the chelating agent or ligand about 0.5 to about 6 hours later. However, the correct timing is no guarantee of success—either with respect to the chemotherapeutic effect of the platinum or the reversing of platinum/enzyme or platinum/—SH interactions—unless the chelating agent has appropriate properties and can be administered by an appropriate route. If the chelating agent or ligand-forming compound is effective in reversing DNA/Pt(II) bonds, the chemotherapeutic effect of the platinum might be reversed even after apparently stable DNA-Pt(II) complexes have been formed. The route of administration can be important also, since acidic aqueous media, conjugating sugars, uronates, glycosides, liver tissue, and other media or agents encountered in living biological systems (and in-vitro systems as well) can inactivate dithiocarbamic toxicity inhibitors of this invention before the inhibitors can bind to the platinum. In experiments with purified DNA, platinum, and alkali metal dialkyldithiocarbamates, it has been found that the dithiocarbamates are sufficiently powerful platinum-binding compounds to dislodge the platinum from Pt/DNA complexes formed in vitro, at very high Pt/DNA ratios. Fortunately, these experiments are not representative of what takes place in vivo. It has now been found that dithiocarbamates do not reverse Pt/DNA binding at normal pharmacologic Pt/DNA ratios.

In contrast, thiourea does reverse Pt/DNA complexes. Nevertheless, thiourea was generally considered one of the most promising "rescue" agents prior to this invention.

It is generally believed that the mechanism of anticancer activity of platinum (II) involves loss of cis leaving groups on the square planar platinum complex followed by or generally simultaneously with an attack upon the DNA helix in the interior of neoplastic cells. One theory is that the Pt(II)/DNA complexes are characterized by crosslinking of DNA chains. The toxic effects of the platinum(II) complexes are presently believed to involve complexing with enzymes which occur in various mammals and other complex multicellular organisms, e.g., in the tubule cells and outer medullary stripe extending into the cortex of the kidney. Among the signs of platinum(II) toxicity are marked increases in blood urea nitrogen (BUN), weight loss, and diarrhea.

It has now been found that the degradation of dithiocarbamic compounds in acid media or other inactivation reactions is not detrimental to the objectives of this invention. Although this invention is not bound by any theory, it is presently believed that various factors may be contributing to the specificity of dithiocarbamic compounds, i.e. their ability to reverse the Pt(II)/—SH bond or other undesired side effects without reversing the Pt(II)/DNA bonds. First, the dithiocarbamic compounds of this invention are believed to be present in vivo as anionic species. It is generally considered to be more difficult for ionic species to penetrate cell membranes, particularly as compared to neutral organic species. (On the other hand, there is some evidence that dithiocarbamates can get into cells, albeit in small amounts.) Second, it is likely that dithiocarbamates simply do not reverse Pt/DNA binding. Third, it appears that the biological half life of the dithiocarbamic compounds of this invention is long enough to provide reversal of Pt(II) side effects. At least two parenteral routes of administration have been found to provide adequate dithiocarbamate half lives, these routes being intravenous (i.v.) and introduction into the peritoneal cavity (i.p.).

Surprisingly, i.v. administration of these dithiocarbamic compounds also inhibits the bond marrow toxicity of platinum compounds present in vivo as platinum-(II) complexes.

To sum up the typical treatment situation as it relates to mammals:

(a) Internal acidic media (e.g. stomach acid) and conjugating compounds within the mammal impose severe half-life limitations upon the "rescue" capability of dithiocarbamic compounds.

(b) If the Pt(II)/—SH or Pt(II)/enzyme reactions are not reversed within six hours of Pt(II) administration, it is unlikely that any "rescue" agent will be effective, and damage from platinum toxicity may become permanent.

(c) Any "rescue" agent which is, however, administered too soon may vitiate the chemotherapeutic effect of the platinum(II) complex.

(d) The "rescue" agent should be ineffective with regard to reversing DNA/Pt(II) bonds formed within cellular DNA.

Parenterally-administered dithiocarbamate compounds of this invention have been found to meet these criteria. The preferred routes of administration avoid excessively short half lives for the rescue agents while leaving the chemotherapeutic effects of the platinum substantially intact. Accordingly, to obtain the desired rescue effects via an oral route of administration, it is presently believed that extremely high dosages of dithiocarbamate or, preferably, some other strategem (acid-resistant blocking groups, acid-resistant encapsulation, or the like) would be needed for adequate rescue effects. For example, the pH of the stomach contents of typical non-ruminant mammals is about 4 or less. At this pH, the dithiocarbamate functional group is rapidly converted to carbon disulfide and an amine or other simple nitrogen compound (e.g. an ammonium salt). The pH of blood in mammals is typically about 3 units higher, which may partially explain the efficacy of the intravenous route. This invention is not bound by any theory, however, and the reason for the extraordinarily high efficacy of the i.v. route is not fully understood. There have been studies in which the chelating behavior of dithiocarbamates has been studied in buffered media, and these studies do not mention any serious half-life problem with the dithiocarbamate functional group.

It is reasonable to conclude that platinum(II) complexes have a variety of useful biological effects. There is evidence that platinum(II) can block the function of the enzyme superoxidedismutase. Pathogenic microorganisms can, under appropriate circumstances, be killed by superoxide build-up. If these organisms have an enzyme system which includes superoxidedismutase, administration of platinum can make the microorganism extremely susceptible to a superoxide kill. Whatever the mechanism which may be involved in the use of platinum against microorganisms, there is evidence indicating that platinum compounds are effective against, inter alia, protozoan parasites. Animals suffering from parasites can apparently be cleared of the disease organism with a platinum treatment; however, the same acute platinum toxicity problems as would be encountered in the treament of cancer occur in this treatment also. In accordance with this invention, dithiocarbamic compounds can provide the means for providing a practical platinum treatment for these disease organisms.

The preferred dithiocarbamic compounds used in this invention will now be described in detail.

DITHIOCARBAMIC COMPOUNDS

It has long been recognized that dithiocarbamic compounds have an extraordinarily powerful capability for complexing with transition metals. In square planar Pt(II) complexes in particular, the

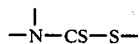

functional group forms one of the most stable Pt(II) complexes known. This functional group has a chelating or ligand-forming effect which is almost impossible to reverse with other chelating agents. Consequently, dithiocarbamic compounds have the ability to substitute for or displace or reverse most other Pt(II) complexes or chelates. Ammonia and amines, for example, are moderately strong ligands in platinum coordinate complexes, but dithiocarbamates can displace them, liberating this free ammonia or amines. Although this invention is not bound by any theory, it is considered significant that both the thiocarbonyl and the thiol sulphurs of the dithiocarbamic functional group can form strong coordinate bonds with platinum. The function of the amido nitrogen in the dithiocarbamic structure is believed to be generally activating in nature, perhaps due to the unbonded electron pair on the nitrogen. Accordingly, it should follow that electron-donating groups substituted on the amido nitrogen should further intensify the activity of the two sulphur atoms. It would also be expected that electron-withdrawing groups substituted on the nitrogen would decrease the activity of the sulphurs. Theoretical studies by many investigators generally confirm these expectations.

Saturated and non-conjugated unsaturated aliphatic and cycloaliphatic groups are known to have a mild electron-donating effect and are particularly suitable for substitution on the amido nitrogen of the dithiocarbamic structure. "Lower" aliphatic or cycloaliphatic radicals, in the context of this invention, are generally considered to be those containing from one to six carbon atoms. These radicals (particularly $C_1$ through $C_3$) do not detract too significantly from solubility of monomeric dithiocarbamic compounds in polar solvents. In addition, these groups do not introduce any acute toxicity aspect to the dithiocarbamic compound. Thus, the preferred dithiocarbamic structure is

wherein $R^1$ and $R^2$ are the same or different and represent electron-donating lower aliphatic or lower cycloaliphatic radicals, or $R^1$ and $R^2$ taken together can form an aliphatic herocyclic ring with the N-atom.

When both $R^1$ and $R^2$ are ethyl, the resulting dithiocarbamic structure has relatively low toxicity and is particularly suitable for administration to living organisms.

For maximum solubility in polar solvents, the preferred dithiocarbamic compounds have the structure

wherein $R^1$ and $R^2$ are as defined previously, and M is an electropositive, ionically bonded metal.

Structures of this type can dissociate into the corresponding dithiocarbamate ion and an $M^+$ cation in aqueous media. Accordingly, pharmaceutically acceptable cations such as the alkali metal cations (particularly sodium and potassium) are preferred.

Given the proper medium for administration (e.g. a suspending rather than dissolving medium), is is not absolutely essential that monomeric dithiocarbamic compounds be used in this invention. The dimer which has the structure

is known to be cleaved in vivo to form the corresponding monomeric dithiocarbamic compounds. In the dimer structure, $R^3$ and $R^4$ are defined in the same manner as $R^1$ and $R^2$.

In summary, the M in the above-described dithiocarbamic structure can be (1) hydrogen, (2) an electropositive, ionically bonded metal, in which case the remainder of the compound is negatively charged, and (3) the second monomer of a dimer.

When $R^1$, $R^2$, $R^3$, and $R^4$ of the dimer are all ethyl, this tetraethyl species is often referred to by its trivial name disulfiram. Disulfiram is commercially available and has been used in the treatment of alcoholism to help the patient remain in a state of self-imposed sobriety. Patients on disulfiram therapy ingesting even small amounts of alcohol experience a highly unpleasant reaction. This alcoholism treatment is carried out by oral administration of disulfiram in tablet form. A disadvantage with disulfiram and similar dimer structures in the context of this invention is their relatively low solubility, particularly in polar solvents. In contrast, diethyldithiocarbamate monomeric salts (e.g. sodium diethyldithiocarbamate) are highly soluble in water, e.g. in molar quantities, and are also soluble in alcohol.

There appears to be no advantage in using the dithiocarbamic acid form of the platinum-binding agents in the context of this invention. These acids generally are soluble in polar solvents such as alcohol, however. In alkaline body fluids, they can be neutralized in vivo to form the corresponding carbamate salts.

Dithiocarbamates and related compounds have been reviewed extensively with respect to their chelating ability in a work by G. D. Thorn et al entitled "The Dithiocarbamates and Related Compounds", Elsevier, New York, 1962. In addition, diethyldithiocarbamate has been successfully used in analytical techniques for measuring Pt(II) in urine; see Borch et al, Analytical Letters B12:917 (1979).

As explained in Chapter 2 of Thorn et al, the preparation of dithiocarbamates is very simple. The compounds of the formula $R^1R^2NCSSH$ or $R^1R^2NCSSNa$ can be formed by reaction of carbon disulfide with a secondary amine, typically in alcoholic or aqueous solution. The usual practice is to carry out this reaction in the presence of NaOH, so that the sodium dithiocarbamate salt is formed. Thus, sodium dimethyl dithiocarbamate is formed from CS₂, NaOH and dimethylamine. See Thorn et al, page 14, and the references cited therein. Although this dimethyl species lacks the optimum solubility and low toxicity characteristic of the diethyl species, it is fully effective in complexing with platinum-(II). The compound sodium N-methyl-N-ethyldithiocarbamate is also known; see Thorn et al, page 16. Other species disclosed by Chapter 2 of Thorn et al include: hexamethylenedithiocarbamic acid, sodium di(beta-hydroxyethyl)dithiocarbamate, various dipropyl, dibutyl and diamyl dithiocarbamates, sodium N-methyl, N-cyclobutylmethyl dithiocarbamate, sodium N-allyl-N-cyclopropylmethyldithiocarbamate, cyclohexylamyldithiocarbamates, dibenzyldithiocarbamates, sodium dimethylene-dithiocarbamate, various pentamethylene dithiocarbamate salts, sodium pyrrolidine-N-carbodithioate, sodium pyrrolidine-N-carbodithioate, sodium piperidine-N-carbodithioate, sodium morpholine-N-carbo-dithioate, alpha-furfuryl dithiocarbamates and imidazoline dithiocarbamates. All of these compounds have excellent platinum-binding properties, the dibutyl, ethyl-methyl, dipropyl, pentamethylene, pyrrolidine and morpholino species being normally preferred in the context of this invention, due, inter alia, to their ability to provide an $R^1R^2NCSS^\ominus$ anion in desired media or bodily fluids. Although this invention is not bound by any theory, it is believed that such anions react with Pt(II) in vivo to form the relatively inocuous compound.

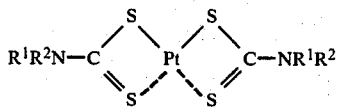

wherein $R^1$ and $R^2$ are as defined previously.

The compounds which appear to be best overall for the purposes of this invention are the

compounds wherein the R groups are lower alkyl radicals. It is also known that diethyldithiocarbamate salts have the ability to reverse the coordination in various coordinate complexes of metals other than platinum. F. W. Sunderman in Ann. Clin. Res. 3:182 (1971) and Ann. Clin. and Lab. Sci. 9:1 (1979) has disclosed a treatment for nickel carbonyl poisoning involving the administration of sodium diethyldithiocarbamate (NaDDTC). This invention, on the other hand, is primarily concerned with mitigating the side effects of platinum compounds deliberately administered to an organism, although the invention does incidentally have utility in the field of treatment of platinum toxicity generally.

SQUARE PLANAR PLATINUM COMPLEXES PRINCIPALLY RELEVANT TO THE CONTEXT OF THIS INVENTION

As is well known in the art of coordination chemistry, the divalent platinum complexes are square planar rather than octahedral, as in the case of tetravalent platinum. Although the detailed mechanism by which square planar Pt(II) complexes exert a toxic effect upon kidneys is not known, comparision of the chemistry and nephrotoxicity of Pt(II) and Hg(II) suggests a possible mechanism. Hg(II) also has a high binding affinity toward sulfhydryl ligands, though not quite the extraordinarily strong affinity of Pt(II). Although this invention is not bound by any theory, it is believed that the brush border of the proximal tubule contains an abundance of protein-bound sulfhydryl or mercapto (—SH) groups; see Cafruny et al, J. Pharmacol. Exp. Ther. 117:101 (1956). E. J. Cafruny in Pharm. Rev. 20:89 (1968) postulates for mercury-induced diureses a mechanism involving reversible inhibition of water and electrolyte reabsorption in the proximal tubule via reversible coordination of Hg(II) to the sulfhydryl group of a membrane-bound transport enzyme. Because of the striking histopathologic similarities between Pt(II) and Hg(II) toxicity in the rat and because of slower rates of ligand exchange in Pt(II) complexes, Borch et al have suggested that the mechanism for cis-platinum(II) nephrotoxicity in the rat involves a concentration-dependent, substantially irreversible binding of Pt(II) to the protein-bound sulfhydryl groups in the proximal tubule with the resulting inhibition of one or more transport enzymes. See Proc. Natl. Acad. of Sci. 76:6611 (1979).

Because of the closely analogous coordinate complexing behavior of various Pt(II) compounds, the concepts of this invention have utility whenever a Pt(II) complex is introduced into a biological system such as complex multicellular organism having kidneys, a digestive system, and similar organs subject to platinum toxicity. Accordingly, the ligands and leaving groups substituted on the square planar complex can vary widely depending upon the reason for platinum administration. If the goal of platinum administration is enzyme inhibition, even the familiar cis-leaving group/cis-diamine structure is not absolutely essential for biological activity. If, on the other hand, the objective is to attack neoplastic cells with a platinum(II) complex, the most active structures are generally considered to be those of the formula:

$$\begin{array}{c} L_3N \\ \diagdown \\ \diagup \\ L_3'N \end{array} Pt \begin{array}{c} X^1 \\ \diagup \\ \diagdown \\ X^2 \end{array}$$

wherein $X^1$ and $X^2$ are the same or different and represent anionically ionizable leaving groups, or, taken together, $X^1$ and $X^2$ can constitute a cyclic difunctional leaving group such as a cyclic dicarboxylic acid; and $L_3$ and $L_3'$ are the same or different and represent residues of ammine or amine ligands, or, in combination, $L_3$ and $L_3'$ together represent the residue of an aliphatic or cycloaliphatic diamine ligand.

A large number of studies have been carried out on complexes of the type described above. These studies suggest that $X^1$ and $X^2$ are preferably leaving groups with greater liability than ammonia or amines (including monodentate amines and bidentate, difunctional amines). Accordingly, $X^1$ and $X^2$ are typically halogens, hydroxyls, carboxyls, and the like.

For a thorough consideration of suitable cis-Pt(II) structures, see Cancer Treatment Reports 63:1433, 63:1493, 63:1499, and 63:1475 (1979). The mechanism of action of the cis-platinum(II) type of complex is discussed in the same journal, volume 63, pages 1439–1443 (1979). See also the aforementioned U.S. Pat. Nos. 4,053,587 and 4,137,248. Of the wide variety of platinum(II) agents described in these studies, cis-dichlorodiammineplatinum(II) is presently believed to be the only species on sale in the United States for any type of antitumor therapy. However, these studies provide evidence that other cis-Pt(II) analogs have activity. Furthermore, Pt(II) compounds can have antibacterial activity even if they do not necessarily have antitumor activity.

According to the literature, preferred antitumor Pt(II) complexes (a) are neutral, (b) contain a pair of cis-leaving groups (generally of intermediate lability, e.g. halogens, oxylates, malonates and other bidentate dicarboxylic acids), (c) two other cis-ligands which are preferably neutral and more or less inert; amine systems (particularly as opposed to oxygen or sulphur dentate groups) are more likely to insure antitumor activity. Other transition metals could theoretically be used in place of platinum, but the best results to date have been obtained with platinum compounds. So long as the cis-leaving groups ($X^1$ and $X^2$ in the structural formula previously set forth) are better leaving groups than ammonia, amines, and similar nitrogen-containing ligands, the exact nature of $X^1$ and $X^2$ does not appear to be critical. (It is desirable that $X^1$ and $X^2$ form physiologically acceptable anions when displaced from the platinum complex.) Accordingly, in addition to the halogen and hydroxyl and carboxylic leaving groups described previously, activity has been observed with sulfato, sulfate, and neutral water molecules.

Of the nitrogen-containing monodentates and bidentates, considerable activity has been shown for ammonia, cyclohexandiamine and its derivatives, alkylene diamines (e.g. ethylenediamine), alkyl-substituted amines, $C_3$ and $C_5$-cycloalkyl amines, and the like. The trans-analogs appear to be inactive against tumors but can still be active against disease-causing microorganisms. Suitably selected tetra valent Pt complexes such as "CHIP" can behave like Pt(II) complexes after administration to a living organism. Removal of axial ligands in vivo accounts for the Pt(II)-like activity, at least to some extent. Such tetravalent Pt complexes can be considered to be compounds of the formula

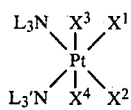

wherein $L_3$, $L_3'$, $X^1$ and $X^2$ are as defined previously, and, as in the structural formula of the Pt(II) complexes described previously, are equatorial substituents of a square-planar complex. The equatorial $X^1$ and $X^2$ substituents are preferably halogens, e.g., Cl. The axial substituents $X^3$ and $X^4$ are the same or different and are similar to $X^1$ and $X^2$ (e.g., halogen, hydroxyl, carboxyl, sulfato, sulfate and neutral water molecules) but are preferably hydroxyls or water molecules. In these Pt(IV) complexes, $L_3N$ and $L_3'N$ are preferably aliphatic amine-type ligands such as $RNH_2$, where R is lower alkyl. A particularly preferred species of Pt(IV) complex is chlorohydroxyisopropylamineplatinum ("CHIP").

"CHIP", like other "second-generation" platinum-containing therapeutic agents is low in kidney toxicity compared to the "first generation" agents but, unfortunately, is high in bone marrow toxicity. The "rescue" technique of this invention also inhibits bone marrow toxicity, however.

Various Pt(II) compounds of demonstrated utility, e.g., "TNO-6" and "CBDCA" (see U.S. Pat. No. 4,137,248) also show increased bone marrow toxicity. These otherwise desirable Pt(II) compounds can be characterized by the formula

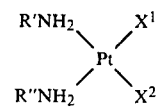

where $X^1$ and $X^2$ are the same or different and are halogen, OH, water, carboxyl, sulfato, or sulfate, or, taken together, the residue of a polycarboxylic acid; $X^1$ and $X^2$ preferably are $SO_3H$ or

particularly as the residue of a polycarboxylic acid such as 1,1-cyclobutane-dicarboxylic acid, trimellitic acid, etc.; R' and R" are the same or different and are halogen or an aliphatic group or, taken together, the aliphatic residue of a heterocyclic moiety which includes both N-atoms.

The diseases treated with platinum(II) complexes are not limited to humans; accordingly, this invention is useful in veterinary medicine. Mice, monkeys, rats, dogs and other species provide good models for the study of Pt(II) or Pt(IV) toxicity and "rescue" agents for ameliorating this toxicity. With respect to the efficacy and toxic effects of cis-platinum(II) in man, rodents (particularly rats) and dogs provide good models. Platinum(II) nephrotoxicity in the rat is characterized by lesions in the proximal tubules which appear to be closely analogous to the same pathologic changes in man observed in the case of either high-dose or low-dose Pt(II) chemotherapy. In addition, suitable tumors are available for inoculation in rat models. The rat is a less suitable model for investigating the efficacy of orally-administered desulfiram; however, it is also possible to administer disulfiram suspensions parenterally. In any event, parenteral routes of administration are preferred.

The median lethal dose ($LD_{50}$) of cis-dichlorodiammineplatinum(II) (DDP) for F344 rats has been reported to be 7.5 mg/kg of body weight. In the context of this invention, effective doses of platinum(II) up to approximately the $LD_{50}$ level can be administered with as much as 100% survival of all treated animals when a suitable dose of the rescue agent is timely administered. The platinum(II) complex can be administered by any of the conventional methods, the intravenous method being preferred.

Typical dithiocarbamic compounds used in this invention are far less toxic than platinum(II). The dialkyldithiocarbamates, particularly diethyldithiocarbamate sodium or potassium salts appear to have the least toxicity in this family of compounds. Parenteral doses on the order of 1,000 mg/kg are considered generally safe. In the case of sodium diethyldithiocarbamate (NaDDTC), rescue efficacy is obtained with lower dosage levels in any event. By the i.p. (intraperitoneal) route, the optimum dosage range appears to be about 500–800 mg/kg. Surprisingly, still smaller doses are effective via the i.v. route, e.g. about 50 to about 400 mg/kg, preferably less than 200 mg/kg. Even after an $LD_{50}$ dose of DDP, an appropriate dose of the rescue agent administered about two hours after the platinum(II) resulted in a sharp drop in nephrotoxicity and gastrointestinal side effects. These results indicate that, not only can these side effects be reduced or substantially eliminated, it is also possible with this invention to relax present limitations on dosages of platinum(II). In humans and other animals, platinum(II) side effects appear to be dos related, and existing protocols mandate dosages which are below acutely toxic levels. Nevertheless, chronic nephrotoxicity has still been observed at these relatively low dose levels. This invention is believed to provide a specific strategy for blocking platinum nephrotoxicity and other side effects in platinum chemotherapy. The treatment strategy of this invention is believed to be significantly superior to vigorous intravenous hydration combined with mannitol diuresis.

The toxicity of NaDDTC is reportedly low ($LD_{50}$ is at least 1,500 mg/kg in rats), and there is at least some history of its use in humans (the treatment for nickel carbonyl poisoning described previously).

In the following non-limiting Examples, toxic side effects of cis-dichlorodiammineplatinum(II) (DDP) were determined through measurements of blood urea nitrogen (BUN) in milligrams per deciliter, weight loss in percent of the animal's weight, observations of any incidence of diarrhea, and microscopic examination of kidneys from sacrificed animals. Urinary excretion of free NaDDTC, total DDTC, and DDTC-glucuronide were determined as described subsequently. Tumor response was determined by measuring mean tumor diameter in centimeters; see Example 2.

EXAMPLE 1

Protecting Experimental Animals Against The Toxic Effects of DDP ("cis-Platinum(II)") With Intraperitoneal NaDDTC and Disulfiram These experiments were conducted with rats, an accepted model for DDP toxicity. Similar dose-related toxic effects have been observed in several animal models and in man. Maximal plasma and urine platinum levels have been observed shortly after a bolus injection of DDP in man and animals, with a rapid initial clearance followed by a second phase of slow clearance. Plasma and urine concentrations generally decrease to less than 10% of maximum levels within 1 to 2 hours.

Materials and Methods

Male F344 (Fischer) rats (average weight, 150 g) were obtained from the Charles River Breeding Laboratory. They were divided into groups of four rats, placed in methacrylate cages, and given National Institutes of Health chow for rodents and water ad lib, for 7 days. Average weight of the rats was 180 g (range, 160-200 g) when injected.

Solutions of DDP (cis-dichlorodiammineplatinum-[II]) were prepared immediately prior to injection in isotonic saline (0.9% NaCl) at a concentration of 1 mg/ml; mannitol (10 mg/ml) was added to duplicate the formulation available for clinical use. Tetraethylthiuram disulfide (disulfiram) was obtained from Sigma Chemical Co., St. Louis, Mo. Sodium DDTC was prepared according to the procedure of Klöpper and van der Kerk, *Rec. Trav. Chim.* 70:917 (1951); immediately prior to injection, it was dissolved in sterile water at a concentration of 100 mg/ml. Sodium bicarbonate was prepared in sterile water at a concentration of 50 mg/ml. All injections were carried out under brief ether anesthesia.

Rats in groups of 8-16 were injected intravenously with DDP at a dose of 7.5 mg/kg (the median lethal dose [$LD_{50}$]); see Ward et al, *Toxicol. App. Pharmacol.* 38:535 (1976). The rats were then randomly divided into two groups; at times from 0 to 6 hours after injection of DDP, one group was injected intraperitoneally with NaDDTC (500 or 750 mg/kg), and the other group was injected intraperitoneally with sodium bicarbonate (370 mg/kg) as a control. One group of rats was given only NaDDTC, in a dose of 750 mg/kg intraperitoneally, to serve as a control for the effects of NaDDTC. In one experiment, blood was obtained from the tail vein for serial daily BUN (blood urea nitrogen) determinations according to Foster et al, *Clin. Chem.* 17:921 (1971). Otherwise, weight and BUN were determined at 5 days after injection, reportedly the time of maximal observed toxicity. Evidence of gastrointestinal toxicity was obtained qualitatively by noting the presence or absence of diarrhea 3-5 days after injection.

Disulfiram was administered to two groups of rats in lieu of NaDDTC, as described subsequently.

Randomly selected animals were sacrificed at 5 days after injection for study of histopathologic changes in the kidney and to note the presence or absence of hemorrhagic enteritis. Kidneys were removed, placed in Zenker's fixative, embedded in paraffin, sectioned at 6 $\mu$m, and stained with hematoxylin and eosin.

Results

Sodium DDTC, at doses of 500 and 750 mg/kg, was given at times ranging from 30 minutes before to 6 hours after administration of DDP; see Table 1, which follows. The rats that received NaDDTC alone maintained normal BUN levels throughout the 2-week period but experienced a mean weight loss of 6% at day 5; by 2 weeks, however, a mean weight gain of 6% was observed. The control animals, which received DDP at 7.5 mg/kg without rescue, experienced a mean weight loss of 21% at 5 days and had a mean BUN level of 234 mg/dl. Serial BUN and body weight determinations in both control and rescued animals confirmed that maximal BUN and weight loss occurred on day 5. Survivors generally showed recovery of both weight and BUN from these extreme levels. Diarrhea was observed in 21 of the 22 animals examined for it. Necropsy revealed a distended membranous small intestine filled with hemorrhagic fluid in every animal examined. Sections of the kidney revealed a pale zone of extensive necrosis and degeneration of tubule cells in the outer medullary stripe extending into the cortex.

Marked reduction in BUN and weight loss were noted when NaDDTC was administered between 1 and 4 hours after DDP, but results for the 6-hour rescue time suggested only minimal rescue efficacy (if any). Diarrhea was not observed in any of these rescued animals. Necropsy revealed a grossly normal small intestine; kidney sections showed a barely discernible pale band of mild tubule degeneration in the outer zone of the outer medullary stripe. When NaDDTC was administered immediately after DDP (time=0 hour), a significant decrease in weight loss was noted without reduction of BUN levels. Rescue 6 hours after DDP administration, however, failed to demonstrate significant reduction either in BUN or weight loss, and two of the five animals in this group were noted to have diarrhea.

Platinum excretion kinetics were measured in four animals by measuring urinary platinum levels every 30 minutes for 4 hours and then every 2 hours for an additional 12 hours. Urinary platinum concentration declined to <10% of maximal concentration within 1.5 hours and >95% of the platinum excreted by the kidneys had appeared in the urine by this time.

In one experiment, disulfiram was administered to two groups of rats at a dose of 2 g/kg via stomach tube 30 minutes before and 30 minutes after DDP. Fifty percent of the animals in each group died before day 5, with grossly hemorrhagic fluid-filled. intestine noted on necropsy. Weight loss and BUN levels in the survivors were highly variable (BUN, 55-180 mg/dl).

These results are believed to demonstrate the salutary effects of NaDDTC rescue on renal function and pathology after a toxic dose of cis-platinum and to strongly suggest a beneficial effect upon gastrointestinal toxicity as well.

For NaDDTC, the rat model appears to be a good one. In any event, it is believed that all species initially present free NaDDTC to the kidney tubule; its site and rate of decomposition depend upon site and rate of urine acidification.

On the basis of these data and our results, we suggest the following rationale for DDP toxicity and NaDDTC rescue. At high plasma and urine platinum concentrations, binding occurs to sulfhydryl groups of the renal tubule; maximal platinum accumulation occurs at 30-60 minutes. Sodium DDTC administered 30 minutes prior to or concurrent with DDP is rapidly metabolized before platinum accumulates, and NaDDTC concentrations after 1 hour are inadequate to remove bound platinum. Rescue between 45 minutes and 4 hours is particularly effective because NaDDTC concentration in the tubular fluid is adequate for platinum chelation and removal. The minimal rescue at 6 hours presumably results from platinum-induced irreversible damage having occurred prior to rescue. Although inhibition of gastrointestinal toxicity generally parallels that observed for nephrotoxicity, the beneficial results of concurrent administration suggest that gatrointestinal toxicity may be more responsive to early rescue.

The variability of results with disulfiram do not negate its efficacy as a rescue agent, but merely suggest that careful technique is needed for the most effective administration.

EXAMPLE 2

Example 1 is believed to demonstrate that intraperitoneal (ip) administration of NaDDTC in doses of 500-750 mg/kg would afford protection from the nephrotoxic effects of DDP at doses as high as 8 mg/kg. The purpose of this Example is to test intravenous (i.v.) as well as ip administration and also to test the effect of NaDDTC on DDP efficacy. Rat mammary tumor 13762 model was selected to determine the effect of NaDDTC on inhibition of tumor growth by DDP. This tumor model is unusual in that spontaneous relapse at the original site occurs approximately 15 days after DDP administration in 25-75% of animals. Although initial tumor response to 2, 4, and 8 mg/kg DDP was identical with or without NaDDTC rescue, local recurrence commenced earlier and tumors grew more rapidly in those animals receiving NaDDTC at intraperitoneal doses of 750 mg/kg.

Intravenous administration was explored in an attempt to deliver larger quantities of free DDTC anion to the likely site of toxicity in the renal tubule; urinary excretion of DDTC was monitored as a means of estimating changes in tubular levels of free DDTC. The standard assay for DDTC anion utilizes a spectrophotometric determination following reaction with cupric ion to form the colored $Cu(DDTC)_2$ complex. Unfortunately, the affinity of cupric ion for sulfur ligands is such that this metal ion will catalyze the decomposition of the DDTC glucuronide and therefore will not discriminate between free and conjugated DDTC. Ferric ion does react selectively with the free ligand, thereby providing a convenient assay for both free and total DDTC in urine.

According to J. H. Stromme in *Biochem. Pharmacol.*, 14:393 (1965), DDTC is rapidly conjugated in the liver.

TABLE 1

| Effects of Sodium Diethyldithiocarbamate (DDTC) Rescue on BUN, Weight Loss, and GI Effects in Rats on Day 5 After cis-Dichlorodiammine Platinum (II) (DDP), 7.5 mg/kg i.v. | | | | | | | |
|---|---|---|---|---|---|---|---|
| DDTC Dose, mg/kg ip | Rescue Time, hours after DDP | n | BUN, mg/dl* | $p^+$ | Weight Loss, %* | $p^+$ | Incidence of Diarrhea |
| 0 | — | 26 | 234 ± 20 | — | 21 ± 1 | — | 21/22 |
| 750 | — | 4 | 16 ± 1 | — | 6 ± 1 | — | |
| 500 | ½ | 4 | 152 ± 20 | <0.05 | 4 ± 2 | <0.001 | |
| 500 | 1 | 4 | 90 ± 5 | <0.001 | 4 ± 1 | <0.001 | |
| 500 | 2 | 4 | 72 ± 11 | <0.001 | 2 ± 2 | <0.001 | |
| 750 | −½ | 4 | 418 ± 43 | <.001 | 18 ± 1 | >0.1 | |
| 750 | 0 | 12 | 214 ± 21 | >0.25 | 9 ± 1 | <0.001 | 0/6 |
| 750 | ¾ | 5 | 56 ± 9 | <0.001 | 8 ± 2 | <0.001 | 0/5 |
| 750 | 1 | 16 | 63 ± 4 | <0.001 | 13 ± 1 | <0.001 | 0/8 |
| 750 | 1½ | 15 | 62 ± 3 | <0.001 | 5 ± 1 | <0.001 | |
| 750 | 2 | 14 | 95 ± 9 | <0.001 | 15 ± 1 | <0.001 | 0/14 |
| 750 | 3 | 10 | 77 ± 8 | <0.001 | 10 ± 1 | <0.001 | |
| 750 | 4 | 7 | 106 ± 8 | <0.005 | 14 ± 1 | <0.001 | |
| 750 | 6 | 5 | 209 ± 44 | >0.3 | 18 ± 2 | >0.1 | 2/5 |

*Mean ± S.E.M. on Day 5
+Significance as compared to controls receiving DDP but not diethyldithiocarbamate, using the Sutdent t test.
Treatment with diethyldithiocarbamate in the absence of cis-dichlorodiammine Platinum (II) (DDP), 7.5 mg/kg i.v.

It was theorized that i.v. administration should therefore be more effective than the oral or intraperitoneal route for delivery of free DDTC to the kidney. Acetazolamide was also investigated as a means for increasing the pH at potential sites of degradation of the DDTC in the kidney. The combination of DDTC and acetazolamide did result in significant increases in renal excretion of DDTC as expected, even when the NaDDTC dose was reduced by 80%. Notwithstanding this increase in urinary DDTC levels, the combination DDP-DDTCacetazolamide was clearly more toxic to rats than DDP-DDTC alone. Accordingly, this Example will focus on the tumor growth studies and upon i.v. administration without acetazolamide.

Materials and Methods

Female F344 (Fischer) rates, initial weight 100–150 g, were obtained from the Charles River Breeding Laboratory, Wilmington, Mass. They were housed in methacrylate cages and given Purina rat chow and water ad libitum for at least one week. Mean weight of the rats were 150 g at the onset of experiments unless otherwise noted.

Solutions of cis-dichlorodiammineplatinum(II) (DDP) were prepared immediately prior to injection in normal saline (0.9% NaCl) at a concentration of 0.2–1.0 mg/ml. Solutions of sodium diethyldithiocarbamate (NaDDTC) (Sigma Chemical Co., St. Louis, Mo.) were prepared immediately before use at a concentration in mg/ml equal to the dose expressed in mg/100 g; thus, injection volumes were identical at all dose levels. Mammary Tumor 13762 was obtained in the form of an implanted tumor in a female F344 rat. All intravenous injections were carried out under brief ether anesthesia.

Tumor inoculation was carried out as follows: two rats bearing tumors having a mean diameter of 2.5–3.5 cm were sacrificed using ether anesthesia. The tumors were excised immediately, finely minced, combined, and resuspended in 20–40 ml of normal saline. This suspension was filtered through a gauze pad to remove coarse pieces of tissue and the resulting suspension inoculated subcutaneously (0.2–0.5 ml/injection) into the left flank of each rat. Tumors were palpable within 7 days in >98% of inoculated animals and generally reached a mean diameter of 2.5–3.5 cm within 10–14 days.

Comparative tumor response experiments were carried out by inoculating randomly selected control and rescue groups with tumor as described above. On day 10, DDP at the appropriate dose was administered intravenously to both control and rescue groups. Two hours after DDP administration, the rescue group was treated with NaDDTC at a dose of 750 mg/kg given intraperitoneally (ip) or 100 mg/kg given intravenously (iv). Tumor size was determined by measuring the longest and shortest diameters with a calipers and recording the arithmetic average. The rats were monitored for 50 days after tumor inoculation or until tumor size exceeded 4 cm. Comparative nephrotoxicity experiments were carried out as described in Example 1. In those experiments using acetazolamide, this drug was administered in a dose of 10 mg/kg intraperitoneally 30 minutes prior to administration of DDP, and rescue was carried out 3 hours after administration of DDP.

Excretion of free and conjugated NaDDTC in the urine of rats was measured as follows. NaDDTC was administered in selected doses via intraperitoneal or intravenous injection. Rats were then placed in metabolic cages and urine was collected and analyzed at 30 minute intervals. Urine samples (0.1–5.0 ml) were added to 2 ml of a solution containing ferric nitrate (20 mM) and sodium citrate (200 mM). The dark $Fe(DDTC)_3$ complex was extracted into chloroform (4 ml) by vortexing for 5 minutes. The mixture was chilled, centrifuged for 1 minute, and the chloroform layer separated. To this chloroform solution was added saturated aqueous cupric sulfate (2 ml), and the mixture was vortexed for 5 minutes, chilled, and centrifuged for 1 minute. The chloroform solution was separated and the $Cu(DDTC)_2$ absorbance measured at 435 nm. Free DDTC was determined by comparison of absorbance to a standard curve. Total DDTC was determined by addition of 0.05–1.0 ml of urine to 3 ml of saturated cupric sulfate followed by incubation at 45° for 30 minutes. The resulting $Cu(DDTC)_2$ complex was extracted into chloroform and analyzed as described above. DDTC-glucuronide excretion was determined by subtraction of free from total DDTC.

Results

DDP was administered on day 10 after injection of tumor cells in doses of 2, 4, and 8 mg/kg to duplicate groups of 8 rats (mean weight 125 g) at each dose level. NaDDTC rescue was carried out 2 hours after DDP administration in one group at each dose level using an intraperitoneal dose of 750 mg/kg. At a DDP dose of 2 mg/kg without rescue, mean tumor size diminished progressively until day 24, when 2/8 rats were tumor free and 6/8 rats bore tumors which reached mean minimum diameter of 1.6 cm. At day 30, mean tumor diameter in these six rats had increased to 2.4 cm. Treatment with 2 mg/kg DDP followed by 750 mg/kg DDTC 2 hours later gave an initial response identical to that of the unreached group; disappearance of tumor was not observed in this rescued group, however, and mean minimum tumor diameter reached 1.2 cm at day 21 with relapse to a mean tumor diameter of 3.0 cm at day 30. The rescue thus leads to an identical initial response but with earlier onset of relapse and more rapid subsequent tumor growth than in the absence of rescue. Qualitatively similar results were obtained at DDP doses of 4 and 8 mg/kg. In the latter case, however, ⅜ rats died as a result of DDP nephrotoxicity and ⅜ were tumor-free by day 28 in the unrescued group; with DDTC rescue there were no deaths and ⅛ was tumor-free by day 28.

When NaDDTC (500 mg/kg) was administered intraperitoneally to rats, total DDTC excreted by the kidneys within 2 hours represented 18–20% of the dose given. Of this DDTC analyzed in the urine, <0.1% of the initial dose was present as the free ligand; the remainder was the S-glucuronide conjugate. Administration of DDTC as an intravenous bolus of 100 mg/kg increased renal free DDTC excretion in the first 30 minutes by five- to tenfold over that observed with a 500 mg/kg intraperitoneal dose.

Comparison of low-dose intravenous vs. high-dose intraperitoneal DDTC rescue showed that protection against nephrotoxicity was essentially equivalent for both routes. DDP (6 mg/kg intravenously) was administered to 3 groups of 8 rats each. The control group received no further treatment, the intravenous group received 100 mg/kg NaDDTC intravenously, and the intraperitoneal group received 750 mg/kg NaDDTC intraperitoneally 2 hours after DDP. Weight loss on day 5 was similar in the three groups (11, 14, and 9%, respectively); diarrhea was noted in ⅛ rats in the control group but was not observed in the intravenous or intraperitoneal groups. Day 5 BUN's for the control, intravenous, and intraperitoneal groups were (mean±SEM) 92±15, 43±5, and 73±4, respectively. Kidney sections from the control group revealed a zone of moderate necrosis and degeneration at the corticomedullary junction similar in type but to a lesser degree than observed in Example 1 at DDP doses of 8 mg/kg. Sections from the intravenous and intraperitoneal rescue groups were very similar and showed mild hydropic changes with occasional evidence of degeneration.

Finally, tumor responses to DDP in the absence of rescue and in the presence of low-dose intravenous and high-dose intraperitoneal rescue were compared. DDP (2 mg/kg intravenously) was administered on day 10 after tumor inoculation. The control group (n=8) received no further treatment; the intravenous (n=8) and intraperitoneal (n=11) groups received NaDDTC 2 hours after DDP in doses of 100 mg/kg intravenously and 750 mg/kg intraperitoneally, respectively. Tumor response in the intraperitoneal rescue group was qualitatively similar to that described previously; minimum tumor diameter (1.3 cm) was reached on day 23 with relapse occurring in 9/11 rats to a mean tumor diameter of 2.2 cm by day 30 (data not shown). Tumor response in the control and intravenous rescue groups, however, were generally equivalent in all respects. Initial response was identical in both groups; relapse was observed in 2/8 rats in each group between days 25 and 30, with the other rats remaining essentially free of tumor through day 50 when the study was terminated.

In short, when 2 mg/kg is the i.v. DDP dose, and 100 mg/kg is i.v. rescue dose, no adverse effects of NaDDTC administration on tumor response to DDP were observed. It appears from these data that sodium diethyldithiocarbamate can be administered intravenously in doses which effectively inhibit platinum-induced nephrotoxicity without deleterious effects on tumor response. The reason for the superiority of the i.v. route of NaDDTC administration over the other parenteral route used in this Example (the ip route) is not understood at this time. The ip route of rescue administration does not seem to have any significant adverse effect upon initial tumor response, but locally recurring tumors recur earlier and grow more rapidly when compared to the results in the DDP/i.v. rescue experiments,

EXAMPLE 3

In accordance with the procedure in Borch et al, Analytical Letters, 12(B8):917–926 (1979), cis-dichlorodiamine platinum(II) (DDP) is complexed with a sodium dithiocarbamate (as in the previous Examples) and recovered from urine by extraction with chloroform. Concentrations of Pt(II) are determined by HPLC (high pressure liquid chromatography). When log (Pt) is plotted against time, as in Borch et al, page 924, similar curves are obtained when the anion of the sodium dithiocarbamate is:
di-n-butyldithiocarbamate
di-n-propyldithiocarbamate
pentamethylenedithiocarbamate
tetramethylenedithiocarbamate

EXAMPLE 4

Sodium DDTC was found to be effective in reducing the toxicity (including bone marrow toxicity) of the following compounds:

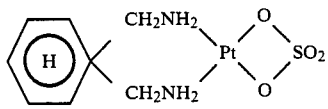

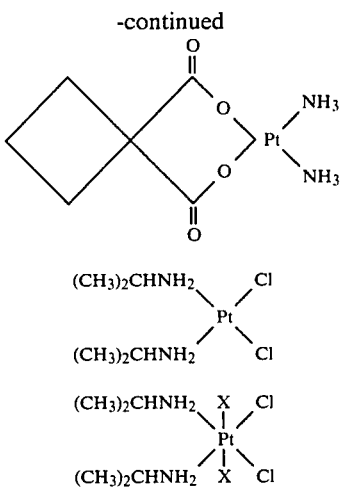

where X=OH or $H_2O$

What is claimed is:

1. A method for inhibiting platinum toxicity in a live mammal being administered a physiologically active but toxic platinum (IV) complex of the formula

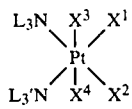

wherein $X^1$, $X^2$, $X^3$ and $X^4$ are the same or different and represent anionically ionizable leaving groups, or, taken together, $X^1$ and $X^2$ can constitute a cyclic difunctional leaving group; and $L_3$ and $L_3'$ are the same or different and represent the residues of ammine or amine ligands, or, in combination, $L_3$ and $L_3'$ together represent the residue of an aliphatic or cycloaliphatic diamine ligand; said method comprising the steps of:

(a) administering to said mammal a said platinum (IV) complex in a physiologically active amount less than the median lethal dose for said mammal;

(b) administering to said mammal, within about 6 hours, but at least 0.5 hours after said step (a), an effective platinum (IV) toxicity inhibiting amount of a platinum binding compound having the formula:

wherein $R^1$ and $R^2$ are the same or different and each represents an alkyl group having up to six carbon atoms, and M is selected from the group consisting of (1) hydrogen, (2) an electro-positive, ionically bonded metal, in which case the remainder of said compound is negatively charged, and (3) the radical

in which case $R^1$ and $R^2$ are also ethyl, whereby such platinum-binding compound is dimeric and is cleaved in vivo to the platinum-binding compound in which M is hydrogen or an electro-positive, ionically bonded metal.

2. A method according to claim 1, wherein the administering of the platinum complex is carried out intravenously.

3. A method according to claim 1, wherein $X^3$ and $X^4$ are $H_2O$ or $OH$ and are axial substituents.

4. According to claim 1, wherein said platinum binding compound is administered parenterally.

5. A method according to claim 4, wherein said platinum binding compound is administered intravenously.

6. A method according to claim 1, wherein, in said platinum-binding compound, M is an alkali metal.

7. A method according to claim 1, wherein said platinum-binding compound is disulfiram.

8. A method according to claim 3, wherein $X^1$ and $X^2$ are halogen and $L_3N$ and $L_3'N$ are $RNH_2$, R being a lower alkyl group having less than 6 carbon atoms.

9. A method according to claim 1, wherein said platinum binding compound is water soluble.

10. A method according to claim 1, wherein, in said step (b) said platinum binding compound is administered intravenously in a dosage ranging from about 50 to about 400 mg/kg of the body weight of the mammal.

* * * * *